(12) United States Patent
Ou et al.

(10) Patent No.: US 6,207,167 B1
(45) Date of Patent: Mar. 27, 2001

(54) CHICKEN LEUCOCYTOZOON VACCINE

(75) Inventors: Jonathan T. Ou, Taoyuan; Chishih Chu, Taichung, both of (TW)

(73) Assignee: Crystal Biotechnology Research and Development Co., Ltd., Taipei (TW)

( * ) Notice: Subject to any disclaimer, the term of this patent is extended or adjusted under 35 U.S.C. 154(b) by 0 days.

(21) Appl. No.: 09/457,072

(22) Filed: Dec. 9, 1999

(51) Int. Cl.[7] .................................................... A61K 39/02
(52) U.S. Cl. ................................. 424/200.1; 424/265.1; 424/269.1; 424/258.1; 530/350; 435/320.1; 435/69.1; 435/69.3; 435/71.1; 435/71.2; 435/172.3; 536/23.7
(58) Field of Search ............................... 435/320.1, 69.1, 435/69.3, 71.1, 71.2, 172.3; 424/258.1, 265.1, 269.1, 200.1; 530/350; 536/23.7

(56) References Cited

U.S. PATENT DOCUMENTS 6,024,961 * 2/2000 Curtiss, III et al. ............... 424/200.1

OTHER PUBLICATIONS

Dunstan et al. Infection Immunity. 67(10): 5133–5141, Oct., 1999.*
Wang et al. Microbial Pathogenesis. 27: 55–9, Jul., 1999.*
Kaniga et al. Infection Immunity. 66(12): 5599–5606, Dec., 1998.*

* cited by examiner

*Primary Examiner*—Jennifer Graser
(74) *Attorney, Agent, or Firm*—Rosenberg, Klein & Lee

(57) ABSTRACT

A vaccine strain OU5758 is provided which includes an attenuated immunogenic plasmidless *Salmonella enterica* serovar-Typhimurium strain OU5046 harboring a recombinant plasmid pOU1500 for immunizing a chicken against leucocytozoonosis. The strain OU5046 is adapted to remain substantially avirulent, survive in vivo for at least a number of days, colonize within the chicken's liver, spleen, ovaries, or other internal organs, and express foreign antigens. The recombinant plasmid pOU1500 contains a gene encoding the circumsporozoite protein of the sporozoite of the chicken leucocytozoonosis parasite *Leucocytozoon caulleryi*. The vaccine strain OU5758 containing pOU1500 is capable of expressing circumsporozoite protein of *L. caulleryi* sporozoite, inducing anti-*L. caulleryi* immunity in chickens when ingested, reducing the frequency and severity of the disease's occurrence, and thereby enabling the chicken to maintain its normal egg production.

12 Claims, No Drawings

CHICKEN LEUCOCYTOZOON VACCINE

BACKGROUND OF THE INVENTION

Chicken suffering from leucocytozoonosis show symptoms of a pale crown, excretion of green feces, loss of the glossy appearance of the feather, internal hemorrhage, malaise, dramatic reduction in egg production, and even death. The etiologic agent of leucocytozoonosis is *Leucocytozoon calleryi*, a protozoan parasite of the chicken and the mosquito, *Cullicoid arakawae*. When the mosquito carrying *L. calleryi* bites the chicken for the blood, the sporozoite of *L. calleryi* in the salivary gland of the mosquito is injected with the saliva into the chicken. The sporozoite migrates to the internal organs such as the liver and spleen, where it proliferates, emerges as schizonts and enters into the blood. The schizont infects the red blood cells, proliferates, and transforms into merozoites, which in turn infects other red blood cells, and proliferates, producing more merozoites. This cycle is repeated several times. Thus, the red blood cells are repeatedly infected and destroyed, and as a result, the chicken becomes anemic and loses the redness of the crown. The merozoites then become gametocytes, which enter the mosquito when the mosquito bites the diseased chicken. The gametocytes in the mosquito mate to form zygotes, which, as they mature, further migrate to the salivary gland, where they transforms into sporozoites, to complete the life cycle.

Many drugs have been used for the treatment of leucocytozoonosis, but most are ineffective except pyrimethamine. Unfortunately, pyrimethamine is not only inducing resistant strains but also carcinogenic and can remain in the egg, so that it would be a health hazard for humans. Therefore, pyrimethamine is prohibited from using in the chicken by the authority. There are no effective drugs available for the treatment of leucocytozoonosis in chicken. Leucocytozoonosis causes damage to the chicken industry and consequently, the damage induces great economic loss. Chicken leucocytozoonosis must be controlled.

An alternative and better approach to deal with a disease is prevention, and the most effective and economical approach is to use a vaccine. There are various types of vaccine, depending on the purpose. Some vaccines induce humoral immunity, i.e., specific antibody, and others induce cellular immunity, i.e., leucocytes. Since the etiologic agent of chicken leucocytozoonosis is a protozoon, Leucocytozoon, the immunization effect of antibody is limited. Furthermore, in order to prepare a vaccine that induces humoral immunity, a large amount of Leucocytozoon must be collected first, and mass production of Leucocytozoon is problematical because it is tedious and difficult. To collect schizonts, merozoites or gametocytes, of Leucocytozoon, for example, a huge volume of infected chicken blood during a certain diseased period must be collected first, and these different stages of Leucocytozoon are then isolated and purified from the blood. To gather sporozoites, one must grow *L. calleryi*, the chicken mosquito, in a large scale, allow them to bite diseased chicken in an appropriate period, and then isolate sprozoites from the salivary glands of these mosquitoes. In either case, the diseased chicken in a certain disease period must be used, because the protozoa in various stages and sporozoite only appear, respectively, in a certain phase of the diseased chicken. Thus, these materials are very difficult to prepare. Furthermore, a vaccine that is against the protozoa in a stage, such as merozoite, will not be effective against the protozoa in other stages, such as sporozoite, because of different antigenecity. Such vaccine, consequently, will not be effective against leucocytozoonosis.

A better approach to protect chicken against chicken leucocytozoonosis is the use of vaccine that can induce cellular immunity. Several considerations must be taken into account in the construction of such vaccine. The first is to determine the target of the vaccine. As described above, there are at least three forms of leucocytozoon in the blood, which means several different antigens. Furthermore, each form has unique and varied antigens. Immunity against a form will not be effective against another form. Thus, a generalized vaccine effective against all leucocytozoon stages in the blood is difficult to make.

When the mosquito injects the leucocytozoon into the chicken it is in the form of sporozoite, which remains so until it reaches the internal organs such as the liver. In contrast to varied antigenecities in the blood, the surface of a sporozoite is largely made up of one antigen, called circumsporozoite (CS) protein, which is very immunogenic. Consequently, CS protein would be a very good vaccine candidate. The next thing one must consider is where to induce the immunity. The internal organs such as the liver are certainly the main candidate location for this, since the destination of a sporozoite is the internal organs. How can the immunity be induced in the liver, or other internal organs? If vaccine could reach the target organs, the immunity could be induced at that organ.

For this purpose, we chose *Salmonella enterica* serovar Typhimurium as the vaccine carrier. The portal of entry of Salmonella such as Typhimurium is gastrointestinal. Typhimurium, furthermore, can cause systemic infection, i.e., it can migrate to the internal organs such as the liver and spleen. Typhimurium is a pathogen, and therefore, one must detoxify Typhimurium (make, it avirulent) before it can be used as a vaccine carrier. However, an avirulent Typhimurium must still retain the ability to migrate to the internal organs, where the immunity must be induced, and must be able to survive, in vivo, for a short period of time. We have obtained such avirulent Typhimurium.

The target of the vaccine is leucocytozoon and therefore, the vaccine must be able to induce the immunity against it. Thus, the vaccine must carry the antigen of sporozoite. To allow a vaccine carrier to carry the antigen, the carrier must contain the gene of the antigen and express it. We are able to clone the CS gene and successfully transfer the CS gene into the vaccine carrier, which expresses the antigen. This is the vaccine.

FIELD OF THE INVENTION

The invention relates to the recombinant plasmid pOU1500 that carries a gene encoding circumsporozoite (CS) protein, strain OU5046 that is a vaccine carrier, strain OU5758 that is derived from OU5046 containing pOU1500 and is the vaccine against chicken leucocytozoonosis, and a method of administering per os (orally) an effective amount of the vaccine to chicken to prevent chicken leucocytozoonosis.

SUMMARY OF THE INVENTION

Therefore, in one aspect, the invention provides a vaccine carrier strain OU5046, a plasmidless and avirulent strain, that is derived from wild type Typhimurium strain OU5045, and that is able to migrate to the internal organs and stays alive, in vivo, for about three days.

In another aspect, the invention provides a recombinant plasmid pOU1500 that contains the circumsporozoite (CS) protein gene, encoding the CS protein of leucocytozoon sporozoite.

In yet another aspect, the invention provides a vaccine strain OU5758 that is a strain OU5046 harboring said vaccine plasmid pOU1500, avirulent yet able to migrate to the internal organs, able to produce CS protein of the leucocytozoon sporozoite, and able to induce the host's immune response against leucocytozoon sporozoite.

In still yet another aspect, the invention provides a method for the prevention of chicken leucocytozoonosis, said method comprising oral administration of an effective amount of the vaccine strain OU5758 to the chicken according to claim 3.

These and other objects as well as features and advantages may be further understood by the following detailed description.

DETAILED DESCRIPTION OF THE INVENTION

As stated above, in one aspect, the invention provides a vaccine carrier strain OU5046 that is characterized as a plasmidless and avirulent strain, derived from wild type *Salmonella enterica* serovar Typhimurium strain OU5045, and able to migrate to the internal organs and stay alive, in vivo, for about three days.

Unlike some enteric pathogens such as Shigella and Vibrio cholerae that stay in the intestine and never leave to other parts of the body after infection, *Salmonella enterica* serovar Typhimurium is able to migrate to the lymph system and internal organs such as the liver and spleen. Therefore, if the Salmonella carries a vaccine antigen such as CS protein, the immunity against the vaccine antigen can be induced at these places, thereby preventing the occurrence of leucocytozoonosis in chicken.

In view of such considerations, the inventors of this patent application selected Typhimurium as the vaccine carrier, since not all serovars of Salmonella can be useful as a vaccine for the chicken, because some are host specific like serovar Typhi that infects only human. In contrast, Typhimurium can infect almost any animal including chicken. Also, Typhimurium is a Salmonella that is pathogenic to many animals including humans, and therefore, an animal immunized with this vaccine can also be immune to Salmonella, often the causative agent of food poisoning, making this vaccine divalent.

Another reason for selecting Typhimurium as the vaccine carrier is its portal of entry, which is gastrointestinal, and therefore, the vaccine must necessarily be a live one. Also, only live bacteria can carry vaccine antigen, and furthermore, only live bacteria (vaccine) can induce cellular immunity, which is an important immunity for the prevention of protozoan infection such as leucocytozoonosis. Conventional vaccine is usually a molecule or dead bacterium that must be administered via injection and the immunity it induces is humoral (antibody). It is rather laborious to inject vaccine to the chicken one by one when there are tens of thousands of chicken. An oral vaccine can be administered by mixing it with the feed or drinking water. This way, it saves time and labor and is also economical.

When such leucocytozoon-live-Typhimurium-oral vaccine is administered to the chicken, it moves to the internal organs such as the liver and spleen, where it induces immunity against leucocytozoon sporozoites. Thus, when the mosquito bites and injects sporozoites and which migrate to the internal organs, the immunity induced in these organs can immediately destroy the sporozoites.

Therefore, the vaccine of the invention comprises an avirulent *Salmonella enterica* serovar Typhimurium strain harboring a recombinant plasmid that carries the CS gene encoding CS protein of leucocytozoon sporozoite and said CS gene can be expressed in said bacteria.

As *Salmonella enterica* serovar Typhimurium is a pathogenic bacterium, the first condition for this strain to be a vaccine carrier is to convert the strain into an avirulent strain incapable of causing illness to the host. However, all virulence factors should not be removed from the vaccine strain, either. The ability of this strain to survive in the host for a short period of time so that the host would have a sufficient time to react and induce immunity, and to migrate to the internal organs so that the immunity can be induced there, must be preserved. The carrier strain OU5046 must therefore possess these requirements: avirulent, short period survivability, and ability to migrate.

Strain OU5046 possessing these essential requirements and useful as the vaccine carrier according to this invention is derived from wild type strain OU5045 by curing the virulence plasmid.

In another aspect, the invention provides a recombinant plasmid pOU1500 that is created with molecular biology by integrating into a carrier plasmid the CS gene encoding CS protein of leucocytozoon sporozoite.

In yet another aspect, the invention provides a vaccine strain OU5758 that is a strain OU5046 harboring said vaccine plasmid pOU1500, is avirulent but has the essential abilities of OU5046, can produce CS protein of leucocytozoon sporozoite, and is able to induce in the host the immunity against leucocytozoon.

In yet another aspect, this invention provides a method for the prevention of chicken leucocytozoonosis, said method comprising the administration per os to chicken of an effective amount of the vaccine strain OU5758 according to claim 3.

This invention will be illustrated further in more detail with the following non-limiting examples.

EXAMPLE 1

Preparation of OU5046, the Carrier Strain

OU5046, the carrier strain, is derived from wild type *Salmonella enterica* serovar Typhimurium strain OU5045. This strain, OU5045, harbors the virulence plasmid, pOU100, that must be removed. This is accomplished by transferring into OU5045 a plasmid called pWR33 from another bacterial strain to replace pOU100. The new strain harboring pWR33 is next treated at an elevated temperature with a chemical agent to chase out pWR33 and a plasmidless new strain, that is the carrier strain, OU5046, is obtained.

EXAMPLE 2

Preparation of a Plasmid Carrying the CS Protein-encoding Gene

The main antigen of the vaccine according to the invention is expressed from the gene responsible for the production of the CS gene of Leucocytozoon sporozoite. Since the surface of leucocytozoon sporozoite is covered mostly by CS protein, there must be abundant CS protein mRNA in Leucocytozoon sporozoite. To obtain CS protein mRNA, *Cullicoid arakawae,* the chicken mosquito, is grown and allowed to suck blood from diseased chicken. Leucocytozoon sporozoites are collected from the saliva of these mosquitoes, and CS protein mRNA is extracted from these Leucocytozoon sporozoites isolated. The CS protein mRNA is converted into cDNA, which is cloned into the carrier plasmid, pBluescript II (+/−) to form recombinant plasmids, which are in turn transferred by electroporation into the above mentioned vaccine carrier strain, OU5046. From the transformants (electroporants) obtained, colony blot method is employed to select the transformants that express CS protein. One of the transformants expressing CS protein is designated as OU5758 and whose recombinant plasmid as pOU1500. OU5758 is further examined to confirm the presence of pOU1500 that contains the CS protein gene insert, and the presence (expression) of CS protein. OU5758 (OU5046/pOU1500) is the vaccine strain of this invention.

EXAMPLE 3

Characterization of Vaccine Strain OU5758

As stated above, OU5758 contains pOU1500 and is capable of producing CS protein. Another essential requirement of a vaccine strain is that it must be avirulent to the animal to be protected. This is tested. The vaccine strain OU5758 and the carrier strain OU5046 (plasmidless, a control) are respectively administered per os to chicken and observed the chicken's state of health for several months. No ill effects are observed throughout the test period. Such no ill effect might be the result of the strain's inability to survive in chicken, that is to say, if the strains are destroyed immediately upon entering chicken, there would be no time to cause ill effect nor to induce immunity. Also, the strain must be able to migrate to the internal organs. Therefore, the strain's (OU5758) migratory ability and survivability are examined. On t=0 day, chicken are administered per os a dose of a million bacteria/chicken. On t=1 (the next day), 2, 3, 4, and 5 days, chicken are sacrificed and their liver is examined for the presence of the strain. In one test, of three chicken examined, one produces 750, another 140, and the third no bacteria. The next day, no bacteria can be seen. In another test, no bacteria are obtained on t=1 day, and on day 2 (t=2), two produced no bacteria and the third 160 bacteria. Thereafter, no bacteria can be observed. This observation indicates that the strain survives in the chicken for at least three days and retains the ability to migrate to the liver, an internal organ.

EXAMPLE 4

The Antigenecity of Vaccine Strain OU5758

The most important feature of a vaccine is, of course, the ability to induce the host's immunity, its purpose. A characteristic of a live vaccine, such as the vaccine of this invention, is to stimulate cellular immunity, and to check the presence of cellular immunity, delayed hypersensitivity test is usually performed. In this test, live antigen is injected subcutaneously into the host, and the following day, the injection site is examined for swelling. If there is a swelling, it shows that cellular immunity is induced. In the present invention, two groups of chicken, one (Group A) a week old and the other (Group B) four months old chicken, are used for this test. Each chicken is administered per os a million OU5758 bacteria and eight days later, live Leucocytozoon sporozoites collected from the saliva of chicken mosquitoes are injected sucutaneously into the chicken wing. The thickness of the wing is measured the next day. The immunized chicken conspicuously shows swelling, whereas the control chicken that is immunized with saline shows negligible swelling. In Student t test, the values of t=2.130, degree of freedom=6, and p=0.05, are obtained in Group A, and in Group B, t=3.6602, degree of freedom=6, and p=0.01<0.02, are obtained. These data indicate that with a dose of a million bacteria per chicken, the vaccine strain OU5758 induces cellular immunity in a week old as well as four months old chicken.

EXAMPLE 5

Efficacy of Vaccine Strain OU5758

From the above observation, it is clear that the vaccine strain OU5758 can activate leucocytes. The aim of a vaccine, however, is to protect the animal from microbial infection. Therefore, the ultimate test of the vaccine strain OU5758 is to see whether or not OU5758 can protect the chicken from developing the disease of leucocytozoonosis by preventing the infection of *Leucocytozoon calleryi.*

Therefore, the following test is performed. Four months old chicken are divided into two groups, a control and experimental, and the latter further divided into four groups. To control group, the carrier strain OU5046 (plasmidless) is administered per os with a dose of five million bacteria per chicken. To experimental groups, the vaccine strain OU5758 is administered per os with doses of $5\times10^6$ to a $10^8$ bacteria per chicken. Two months later, each chicken is challenged with 4,000 live Leucocytozoon sporozoites injected intravenously. The number of live Leucocytozoon sporozoites, 4,000, used in the challenge is 40 fold of the $ID_{50}$ of this parasite. $ID_{50}$ is the dose required to induce leucocytozoonosis in 50% of the chicken. The chicken are observed for 19 days of the egg producing period for (1) appearance of pale crown, (2) excretion of green feces, and (3) the amount of egg production. These three phenomena are typical symptoms of the diseased chicken that developed leucocytozoonosis. A representative result is shown in Table 1. The chicken of control group have all developed leucocytozoonosis as evidenced by the appearance of pale crown and green feces. The experimental groups also show leucocytozoonosis occasionally but the frequency and number are rather low and the disease symptoms light. The most clearly seen effect is in the egg production: control group shows about 16% lower egg production compared to the experimental groups. During the ten days of the most severe disease period, the egg production of the control group is more than 18% lower than the experimental groups.

It can be seen that the efficacy of the vaccine strain OU5758 in preventing *Leucocytozoon caulleryi* infection, hence leucocytozoonosis, is excellent and a dose of $5\times10^6$ OU5758 bacteria appears to be sufficient for the efficacy, though lower dosages have not been tested.

Many changes and modifications in the described embodiment of the invention can, of course, be made without departing from the scope thereof Accordingly, to promote the progress in science and the useful arts, the invention is disclosed and intended to be limited only by the scope of the appended claims.

Deposit Information

*Salmonella enterica* serovar Typhimurium Strain OU5758 was deposited with the American Type Culture Collection (ATCC) 10801 University Boulevard, Manassas, Va., 20110-2209, USA on Oct. 18, 1999 under the provisions of the Budapest Treaty of the International Recognition of the Deposit of Microorganisms for the purpose of Patent Procedure under Accession No. PTA-853.

*Salmonella enterica* serovar Typhimurium Strain OU5046 was deposited with the American Type Culture Collection (ATCC) 10801 University Boulevard, Manassas, Va., 20110-2209, USA on Oct. 18, 1999 under the provisions of the Budapest Treaty of the International Recognition of the Deposit of Microorganisms for the purpose of Patent Procedure under Accession No. PTA-854.

TABLE 1

Efficacy of the vaccine OU5758*

| Chicken Group | No. of Chicken | No. of Eggs Produced (19 days) | Average No. of Eggs per Chicken | Health State of Chicken |
|---|---|---|---|---|
| Control | 6 | 82 | 13.7 | For 5 post challenge days, all chicken appeared normal; thereafter, pale crown has appeared in all. Pale crown appeared for 3 days in two, and the rest 1 day. Also, except for the last 3 days, all excreted green feces. The rate of egg production was conspicuously lowered. |
| Experimental (B22) | 6 | 94 | 15.7 | On day 11, all chicken showed pale crown for 1 day and excreted green feces; however, the egg production. was normal. |
| Experimental (C22) | 6 | 97 | 16.2 | There were occasional green Feces excreted; otherwise all were normal including egg production. |
| Experimental (D22) | 6 | 102 | 17.0 | Green feces were seen in 2 days in the initial 8 days; otherwise all normal. Thereafter, green feces were seen for five days, but there was no appearance of pale crown and the egg production was also normal. |
| Experimental (E22) | 11 | 182 | 16.5 | The health states and phenomena were similar to those of Group D22. |

*Each chicken of 4 months old was administered per os with OU5046 (plsmidless, control) and OU5758 at a dose from $5 \times 10^6$ (control and groups B22, E22) to $10^8$ bacteria/chicken ($5 \times 10^7$ group D22, $5 \times 10^8$ C22). Two months later, the chicken were challenged with 2,000 live sporozoites per chicken injected per intravenous, and the chicken were observed for 19 days for (1) appearance of pale crown, (2) excretion of green feces, and (3) production of eggs. These three phenomena are typical symptoms of leucocytozoonosis. The rate of egg production of control group was about 16% lower that that of experimental groups.

What is claimed is:

1. A vaccine for the immunization of a chicken against leucocytozoonosis comprising:
  (a) a carrier strain OU5046, ATCC Patent Deposit Designation PTA-854, said carrier strain OU5046 being a plasmidless strain of *Salmonella enterica* serovar Typhimurium viable in vivo for at least a predetermined number of days and adapted to migrate to an internal organ of the chicken; and,
  (b) a recombinant plasmid pOU1500 harbored by said carrier strain, said recombinant plasmid pOU1500 including therein a gene encoding circumsporozoite protein of *Leucocytozoon sporozoite*.

2. The vaccine as recited in claim 1, wherein said vaccine is strain OU5758, ATCC Patent Deposit Designation PTA-853, substantially avirulent and orally administrable to the chicken.

3. The vaccine as recited in claim 2 wherein said carrier strain OU5046 of said vaccine strain OU5758 is adapted to remain viable in vivo for at least three days.

4. A vaccine for the immunization of a chicken against leucocytozoonosis comprising a vaccine carrier strain harboring a recombinant plasmid pOU1500, said recombinant plasmid pOU1500 including therein a gene encoding circumsporozoite protein of *Leucocytozoon sporozoite*.

5. A vaccine for the immunization of a chicken against leucocytozoonosis comprising a vaccine strain OU5758, ATCC Patent Deposit Designation PTA-853, said vaccine strain OU5758 comprising:
  (a) a carrier strain OU5046, ATCC Patent Deposit Designation PTA-854, said carrier strain OU5046 being a plasmidless strain of *Salmonella enterica* serovar Typhimurium substantially avirulent to the chicken, said carrier strain OU5046 being adapted to remain viable in vivo for at least a predetermined number of days, and to migrate to at least one internal organ of the chicken; and,
  (b) a recombinant plasmid harbored by said carrier strain, said recombinant plasmid containing a pathogen antigen gene product for stimulating an immune response to the onset of leucocytozoonosis within the chicken.

6. The vaccine as recited in claim 5 wherein said recombinant plasmid includes pOU1500 containing said pathogen antigen gene product.

7. The vaccine as recited in claim 6 wherein said pathogen antigen gene product includes a gene encoding circumsporozoite protein of *Leucocytozoon sporozoite*.

8. The vaccine as recited in claim 7 wherein said carrier strain OU5046 of said vaccine strain OU5758 is adapted to remain viable in vivo for at least three days.

9. A method of immunizing a chicken against leucocytozoonosis comprising the steps of:
  (a) establishing a vaccine strain OU5758, ATCC Patent Deposit Designation PTA-853, harboring a recombinant plasmid pOU1500 including therein a gene encoding circumsporozoite protein of *Leucocytozoon sporozoite*; and,
  (b) orally administering to the chicken a predetermined dose of said vaccine strain OU5758.

10. The method as recited in claim 9 wherein said step of establishing a vaccine strain OU5758 comprises the steps of:
  (a) establishing a prototrophic strain of *Salmonella enterica* serovar Typhimurium; and,
  (b) curing from said prototrophic strain a virulence plasmid to form a plasmidless carrier strain OU5046 ATCC Patent Deposit Designation PTA-854, substantially avirulent to the chicken and adapted to remain viable for at least a predetermined number of days and migrate to an internal organ of the chicken.

11. The method as recited in claim 10 wherein said step of establishing a vaccine strain OU5758 comprises the steps of:
  (a) isolating *Leucocytozoon sporozoites* from the saliva of a mosquito infectiously exposed to leucocytozoonosis;
  (b) extracting circumsporozoite protein mRNA from said *Leucocytozoon sporozoites*;
  (c) converting said circumsporozoite protein mRNA to circumsporozoite protein cDNA;
  (d) forming a recombinant plasmid by cloning said circumsporozoite protein cDNA into a carrier plasmid pBluescript II (+/−); and,
  (e) transferring said recombinant plasmid into said carrier strain OU5046 by electroporation.

12. The method as recited in claim 9 wherein said step of establishing a vaccine strain OU5758 comprises the steps of:
  (a) isolating *Leucocytozoon sporozoites* from the saliva of a mosquito infectiously exposed to leucocytozoonosis;
  (b) extracting circumsporozoite protein mRNA from said *Leucocytozoon sporozoites*;
  (c) converting said circumsporozoite protein mRNA to circumsporozoite protein cDNA;
  (d) forming a recombinant plasmid by cloning said circumsporozoite protein cDNA into a carrier plasmid; and,
  (e) transferring said recombinant plasmid into a carrier strain by electroporation.

\* \* \* \* \*